United States Patent [19]

Nudelman et al.

[11] Patent Number: 5,200,819
[45] Date of Patent: Apr. 6, 1993

[54] MULTI-DIMENSIONAL IMAGING SYSTEM FOR ENDOSCOPE

[75] Inventors: Sol Nudelman, Avon; Donald R. Ouimette, Plantsville, both of Conn.

[73] Assignee: The University of Connecticut, Farmington, Conn.

[21] Appl. No.: 835,761

[22] Filed: Feb. 13, 1992

Related U.S. Application Data

[60] Division of Ser. No. 472,646, Jan. 30, 1990, Pat. No. 5,109,276, which is a continuation-in-part of Ser. No. 199,997, May 27, 1988, Pat. No. 4,938,205.

[51] Int. Cl.$^5$ .................. A61B 1/04; H04N 13/00
[52] U.S. Cl. ............................... 358/98; 358/88
[58] Field of Search ........... 358/98, 88, 901, 100, 358/91, 92; 128/4, 6

[56] References Cited

U.S. PATENT DOCUMENTS 4,873,572 10/1989 Miyazaki et al. ............... 358/98
4,935,810 6/1990 Nonami et al. ............... 358/98

Primary Examiner—Victor R. Kostak
Attorney, Agent, or Firm—Chilton, Alix & Van Kirk

[57] ABSTRACT

An image acquisition system employs elemental and/or lateral effect detectors in conjunction with an optical scanner which provides a beam of radiation tracing out a raster to illuminate an object. The system generates an electrical signal which is processed to generate data indicative of a two or three dimensional image of an object, in spectrally selective monochromatic wavelengths or broadband regions. An endoscope is designed to make particular use of this image generating system. The image system includes a digital system able to provide a data matrix of two and three dimensional coordinates and the radiation intensity at each of the coordinates as well as spectral dependent image processing, display and archival storage.

5 Claims, 10 Drawing Sheets

MULTI-DIMENSIONAL IMAGING SYSTEM FOR ENDOSCOPE

CROSS-REFERENCE TO RELATED APPLICATIONS

This application is a division of U.S. application Ser. No. 472,646 filed on Jan. 30, 1990, now U.S. Pat. No. 5,109,276, which is a continuation-in-part of International Application PCT/U.S. 89/02322 filed on May 26, 1989, which is a continuation-in-part of U.S. application Ser. No. 199,997 filed on May 27, 1988, now U.S. Pat. No. 4,938,205.

BACKGROUND OF THE INVENTION

1. Field of the Invention

This invention relates generally to three dimensional electronic imaging systems. This invention also relates generally to endoscopes, which are employed in medicine for imaging selective body regions and for facilitating the delivery of high-energy radiation for treatment purposes. More particularly, the present invention relates generally to endoscopes which employ fiber optic channels and which employ lasers or other high-energy radiation sources.

2. Prior Art and Pertinent Technology

Stereoscopy is a function of the mental interpretation of two slightly different images viewed by the two eyes of an observer. The mental interpretation is based on the experience of the observer. Stereo imagery has been demonstrated on television systems. The stereo images are shown on the television display with one perspective displayed in even fields and the other perspective displayed in odd fields. Special glasses are employed so that one eye of the observer views the even fields and the other eye views the odd fields. The cognitive faculties of the observer processes the two dimensional images to provide a perceived three dimensional image.

Stereo image acquisition has been obtained by numerous techniques. One technique disclosed in an article by Yakimovsky and Cunningham entitled "A System for Extracting Three Dimensional Measurements from a Stereo Pair of TV Cameras", published in *Computer Graghics and Image Processing* 7, page 195-210, 1978, employs a stereo pair of TV cameras which are precisely laterally spaced so as to obtain a stereo perspective at a desired distance. In X-ray diagnostic radiology, the X-ray source may be displaced from one position to another position for two successive exposures. The radiation sensor is stationary. The two images are conventionally filmed. The film images can be viewed on a typical stereoscope. The images can also be read into a digital video system for viewing on a stereo video display such as described above. In conventional stereo imagery, the object is uniformly illuminated and the images are acquired entirely in a two dimensional format—typically by means of photographic film or a TV camera.

In conventional stereo imaging, correlating and calculating the data obtained from two stereo images to extract the third dimension or elevation (depth) information, is a fairly complex task which ordinarily involves extensive post detection processing. Conventional stereo imaging techniques employ two images taken at slightly different angles from the object. A cross-correlation number then is applied to the two images for determining the lateral shift of each pixel in the image. The lateral shift corresponds to the displacement (third dimension) of the given pixel for the object. The processing procedure is limited by the ability to cross-correlate pixels from the two different images. Objects having low contrast and very little high frequency detail frequently result in a significant amount of ambiguous correlation. In addition, the processing is a computationally exhausting task—especially for large images.

For some applications, the size of the image sensing components is of paramount importance. Typically stereo imaging requires two photographic or video cameras. The video cameras may take the form of conventional video tubes or solid state CCD chips. Even though the CCD chips have a relatively small size, the CCD chips are not practical for use in acquiring stereo images in applications such as those requiring small diameter endoscopes.

The new and improved endoscope and associated system of the present invention has particular applicability in medicine for many procedures such as those that use a gastroscope, sigmoidoscope, uretheroscope, laryngoscope, and bronchoscope. The invention also has applicability in connection with industrial applications, such as, for example, remote focus flexible fiberscopes, micro-borescopes, and micro-fiberscopes.

Conventional endoscopes typically employ incoherent bundles of optical fibers for transmitting light rays (typically white light) from a proximal end of a tubular instrument to the distal end. Typically, a pair of diametral channels are employed for illuminating an object to be imaged. A separate coherent flexible fiber optic channel communicates from the distal end to the proximal end with an eyepiece, television camera, photographic camera or other imaging devices for providing an image. For relatively large diameter endoscopes, a separate flexible-fiber quartz channel may be employed for transmitting a high-powered beam of laser radiation to an object for therapeutic purposes. An auxiliary channel may traverse the tubular endoscope for receiving various instruments for severing and retrieving selected tissue. In addition, the endoscope may contain channels which provide for water and air communication with the distal end of the endoscope.

Conventional endoscopes provide a reasonably high quality image-especially in large diameter endoscopes. Conventional endoscopes are quite versatile and perform a large variety of useful functions. The conventional endoscopic optic systems, however, do exhibit a number of deficiencies. When viewing objects under high resolution, the image may exhibit a mesh of chicken-wire effect wherein individual groupings of fibers are outlined. Conventional endoscopes also exhibit some degree of loss of contrast associated with scatter intrinsic to the illumination of the object, and also some loss of contrast due to veiling glare of the multiple optical components. The space requirements, e.g., the diameter of the endoscope, represents a design constraint which is significant when separate illumination and imaging channels are employed. Such a constraint may be quite critical for vascular endoscopes which image interior arteries having diameters on the order of two millimeters or less. Another constraint of the conventional endoscopic optic systems is that they do not provide an optical system which facilitates stereo or three dimensional imaging, or the opportunity to acquire multi-spectral-multi-dimensional images, simultaneously.

The imaging channel of a conventional endoscope may be coupled to a television camera or the television camera may be employed in conjunction with an eyepiece by means of an optical beam splitter. The video signal output from the television camera is fed to a television monitor and/or a video recorder of a digital image acquisition system for processing, display and archival storage. The television camera may be a conventional television tube, a solid state video camera employing CCD chips, or other conventional forms.

Sato U.S. Pat. No. 4,604,992 discloses a CCD video camera chip at the distal end of the endoscope. The disposition of the CCD chip obviates the use of the coherent fiber optic bundle for imaging, and thus, provides a system which produces an image not susceptible to the chicken-wire effect or to individually broken fibers which cause pixel dropout. The size of the CCD chip, however, limits the minimal diameter of the endoscope. The CCD video camera chip as well as conventional endoscopes also allow for the passage of high energy laser radiation through auxillary channels to be trained on the object for therapy while the object is concurrently viewed through the CCD imaging camera.

Karaki et al U.S. Pat. No. 4,808,636 discloses a solid state type of imaging sensor positioned at the proximal end of the endoscope. The analog video signal is converted to a digital signal. The digital signal is then processed to eliminate the chicken-wire or mesh effect and to account for the pixel dropout in the displayed image. Pixel dropout commonly results from broken fibers in the fiber optic bundle. The spacial resolution for the conventional endoscope is essentially determined by the diameter of the optical fibers and the magnification of the imaging optics. In general, the commonly employed fibers have diameters in the range of eight to ten microns for high-resolution endoscopes.

Lateral effects photodiodes are routinely employed as position sensors for applications in which a light source can be attached to the object of interest. The lateral effect diodes are capable of resolving the position of an incident light spot to thereby determine the position of the object. In automated manufacturing operations, electronic systems which employ lateral effect photodiodes are used to track robot arms and other objects that are involved in the manufacturing process.

Other references which are related to the general field of the invention are identified by patentee and patent number as follows:

| Mok | U.S. Pat. No. 4,641,650 |
|---|---|
| Murakoshi and Yoshida | U.S. Pat. No. 4,473,841 |
| Murakoshi and Ando | U.S. Pat. No. 4,562,831 |
| Toida et al | U.S. Pat. No. 4,550,240 |
| Pinnow and Gentile | U.S. Pat. No. 4,170,997 |
| Loeb | U.S. Pat. No. 4,418,688 |
| Kanazawa | U.S. Pat. No. 4,418,689 |
| Ogiu | U.S. Pat. No. 4,419,987 |
| Epstein and Mahric | U.S. Pat. No. 4,011,403 |
| Barath and Case | U.S. Pat. No. 4,589,404 |
| Kato et al | U.S. Pat. No. 4,706,118 |
| Takano | U.S. Pat. No. 4,454,882 |
| Sheldon | U.S. Pat. No. 3,499,107 |
| Sheldon | U.S. Pat. No. 3,021,834 |
| Sheldon | U.S. Pat. No. 2,922,844 |

SUMMARY OF THE INVENTION

Briefly stated, the invention in a preferred form, is an image acquisition system for acquiring three dimensional images of objects. An optical scanner with a source generates a beam of non-ionizing electromagnetic radiation for tracing out a raster. A coherent fiber optic cable is optically coupled to the scanner for illuminating an object with the raster. For two and three dimensional imaging a lateral effect photodetector detects radiation which is reflected from the object. Signals from the photodetector communicate with an electronic processor for determining the position of detected radiation relative to the photodetector and for generating topographic data indicative of a three dimensional image of the object. A pair of spaced lateral effect photodetectors may also be employed. For two dimensional imaging and spectrally selective imaging, conventional elemental photodetectors can be used with or without lateral effect photodetectors.

The processor generates a data matrix of three dimensional coordinants and the detected intensity of radiation which is reflected from the object. One or more additional photodetectors may be employed for detecting the radiation intensity. The data may be transmitted to a video display for displaying multiple perspective views of the object. Filters may be employed in connection with the photodetectors so the photodetectors are spectrally selective The signals from the photodetectors are amplified and can be converted into a digitized format.

The invention in one form is a new and improved endoscope which incorporates a modified optical system for the endoscope, an optical scanner and an elemental detector-video system. The optical system is designed in one embodiment to employ a single coherent fiber-optic channel which can be used for both illumination and imaging. The endoscopic optical system, in conjunction with the optical scanner, permits the acquisition of images with improved contrast, improved spacial resolution, improved speed of response, the delivery of an independent beam of radiation directed precisely to a selected location of the object, multi-dimensional and multi-spectral imaging.

An endoscope in one embodiment comprises a bundle of coherent flexible optical fibers which form an optical channel. An elemental photodetector generates an electrical signal having an instantaneous value which is proportional to the quantity of light which impinges on the photodetector. The endoscope is adapted for operation in association with an optical scanner which generates a beam of radiation tracing out a raster. The raster from the scanner traverses a beam splitter and is projected on the proximal end of the optical channel. The light raster traverses the optical channel and is projected through the distal end of the optical channel for illuminating the surface of an object to be examined. Radiation reflected from the surface traverses back through the optical channel and is directed by the beam splitter to the photodetector. A second therapy beam may also be projected on the proximal end of the optical channel for traversal through the channel. The photodetector may be selectively responsive to a pre-established narrow band of the electromagnetic spectrum.

In another embodiment, the endoscope comprises a bundle of coherent flexible optical fibers forming a first optical channel which extends the length of a flexible tubular probe. At least one incoherent flexible optical channel is received in the probe and diametrically spaced from the first optical channel for transmitting reflected optical radiation. Elemental photodetectors optically communicate with the incoherent optical channels and generate electrical signals having instantaneous values proportional to the quantity of light which impinges the photodetectors. Two coherent optical channels may be provided and a lateral effect photodiode associated with each channel generates signals indicative of a topographic image of the surface of the object being examined.

In another embodiment, the endoscope has one coherent flexible fiber optical channel and at least one elemental photodetector is mounted at the distal end of the probe for sensing reflected radiation from the object under examination. The optical fibers of the optical channel may have the general shape of an elongated truncated cone wherein the diameter of the fibers at the proximal end of the cone is significantly greater than the diameter of the fibers at the distal end of the cone. The proximal end surface of an optical channel may be defined by a substantially rigid connected bundle of fibers having a generally cylindrical shape, and the distal end surface of the optical channel may be defined by a rigid substantially connected bundle of fibers having a generally cylindrical shape. The raster which is projected on the proximal end of the optical channel has a boundary which defines a central fiber region and an outer fiber region of the optical bundle. Photodetectors can be mounted at the proximal end for optical communication with optical fibers in the outer fiber region. Radiation reflected from the surface of the object being examined is transmitted through optical fibers of the outer fiber region, thereby permitting illumination and signal read out in a concentric manner.

An object of the invention is to provide a new and improved system for electronically acquiring multi-dimensional images.

Another object of the invention is to provide a new and improved imaging system which employs one or more relatively compact detectors for acquiring multi-dimensional imagery.

Another object of the invention is to provide a new and improved imaging system for acquiring multi-spectral multi-dimensional images capable of efficient correlation with object features such as texture, growth characteristics and spectra.

Another object of the invention is to provide a new and improved endoscope combined with a video optical scanner system therefor which does not require a separate illumination channel.

Another object of the invention is to provide a new and improved endoscope which facilitates the derivation of stereo pairs and three-dimensional imaging of the surface to be illuminated.

A further object of the invention is to provide a new and improved endoscope having a compact and efficient form which is adapted for use with a second beam of optical radiation.

A further object of the invention is to provide a new and improved endoscope and associated optical scanner system which is capable of imaging with one light or laser source while one or more other sources are employed simultaneously for therapy or other diagnostic purposes.

A further object of the invention is to provide multi-spectral imaging with or without multi-dimensional imaging.

Other objects and advantages of the invention will become apparent from the drawings and the specification.

DETAILED DESCRIPTION OF THE INVENTION

Figure 1:
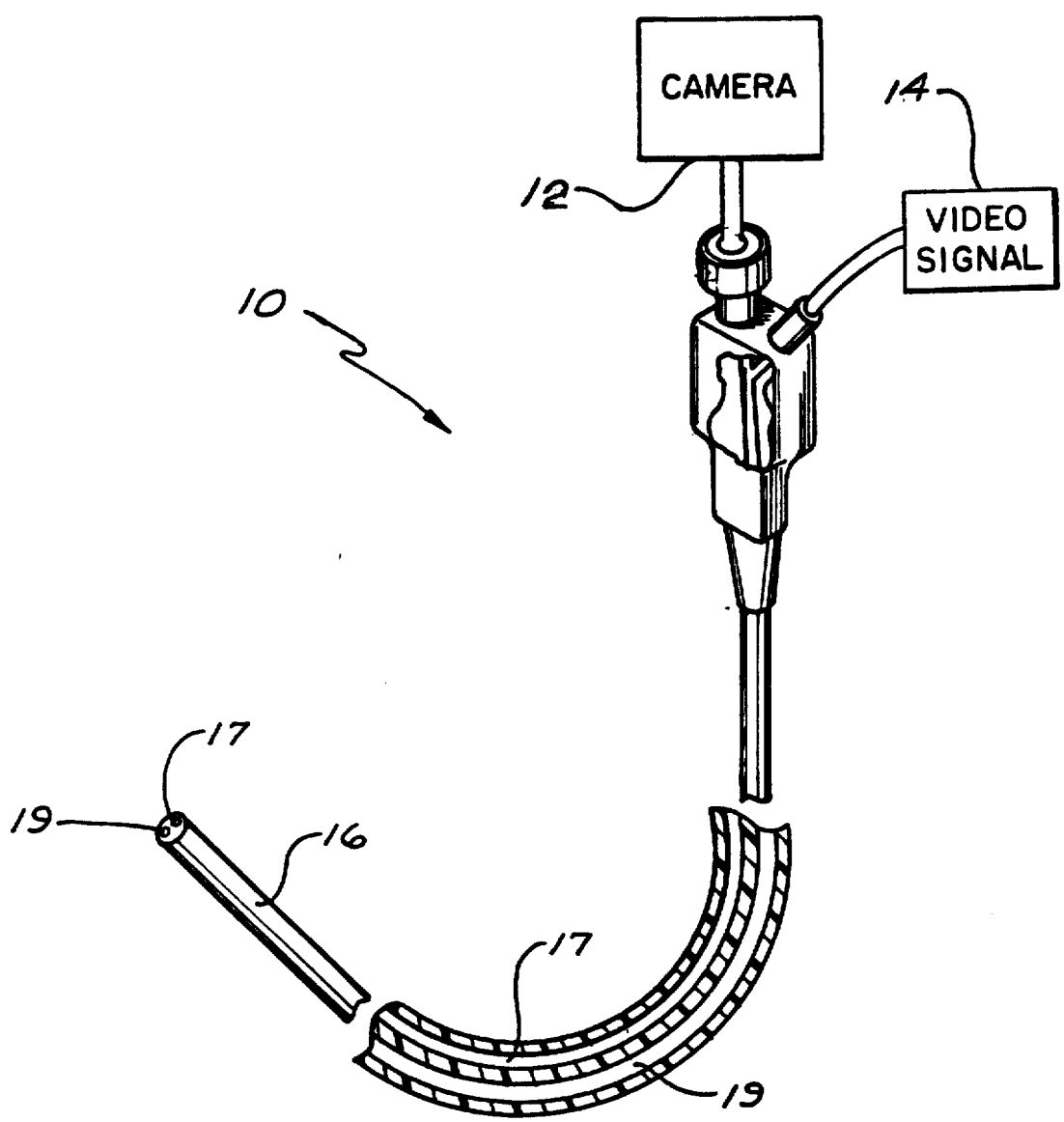
FIG. 1 is a side view, partly broken away and enlarged to show section and partly in schematic, illustrating a new and improved endoscope in accordance with the present invention.

With reference to the drawings wherein like numerals represent like elements throughout the figures, an endoscope in accordance with the present invention is generally designated by the numeral 10 in FIG. 1. A video optical scanner camera (schematically illustrated) designated generally by the numeral 12 is optically coupled to the endoscope. Scanner camera 12 contains a laser or a white light source. The endoscope 10 is especially adapted for use in conjunction with a video optical scanner camera which traces out a raster of illuminating light. The endoscope 10 has means for extracting a video signal 14 and an elongated flexible tubular probe 16 which is insertable into the body of a patient for examination and therapy purposes. The resulting endoscopic system, as will be hereinafter described, generates high speed, essentially lag-free images having a high resolution and wide dynamic range. The endoscopic system exhibits reduced scatter and reduced veiling glare and is adapted for spectral dependent tomography and multi-dimensional imaging including simple stereo projections. The endoscope probe 16 may be embodied in a relatively compact configuration which is dimensionally compatible with conventional, smaller diameter endoscopes. Probe 16 carries the coherent fiber optic channel 17. Another channel 19 of the probe might constitute a flexible tube through which a medical instrument, such as a biopsy tool can be passed.

Figure 3:
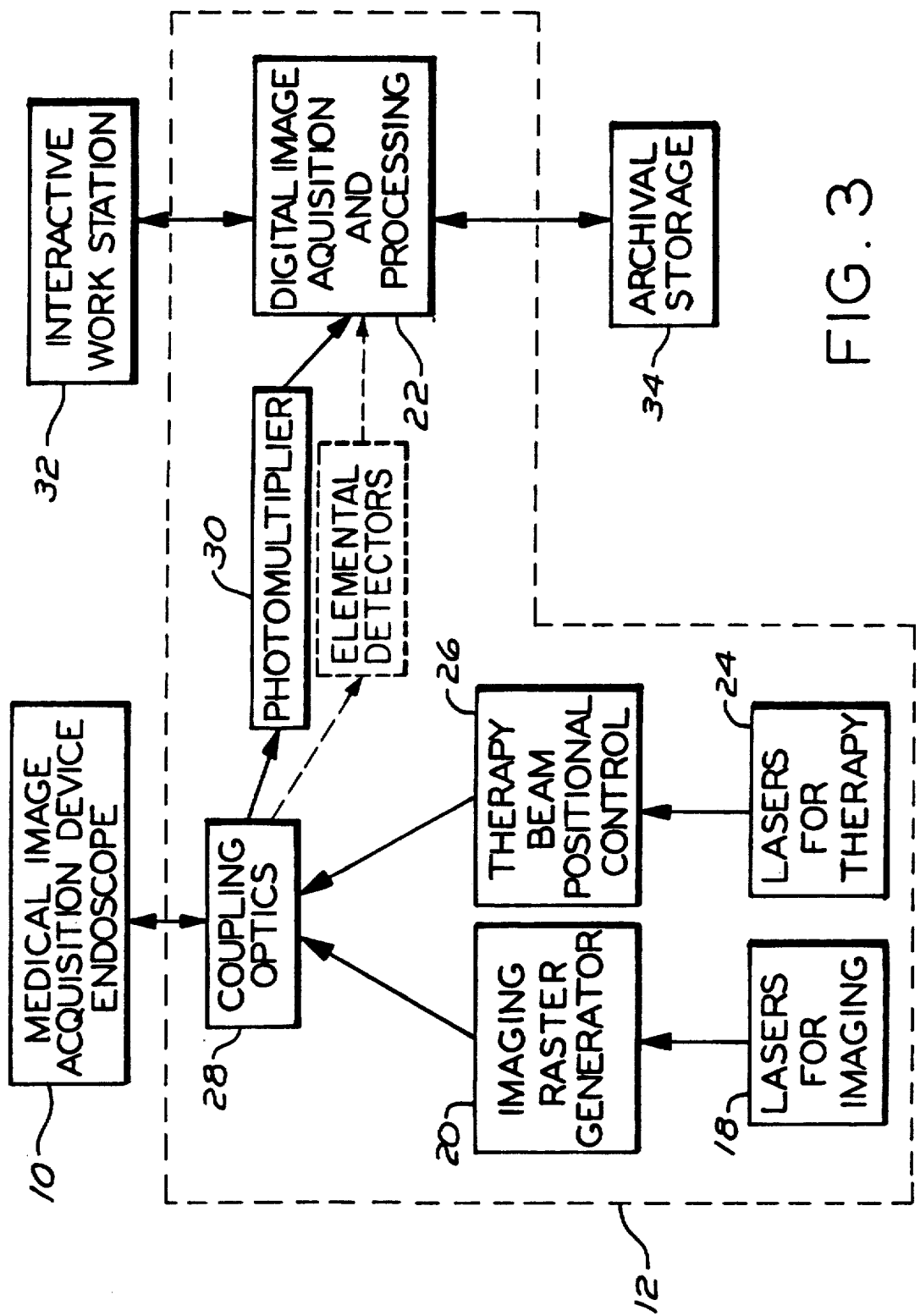
FIG. 3 is a schematic block diagram of the endoscope and the video camera system of FIG. 2.

With additional reference to FIG. 3, the video optical scanner camera 12 may be any of a number of conventional types. In preferred form, the camera 12 functions by projecting an optical raster of light onto the surface of an object. The camera senses the reflected radiation with an elemental photodetector to generate a video signal. Preferred cameras employ lasers 18 as a source of radiation although other non-laser sources can also be employed in connection with the invention. An associated raster generator 20 is optically coupled to laser 18 for generating an illuminating raster. As described herein, the invention is described in terms of a laser source of illumination for the object to be examined and imaged. The advantages of a laser source include a wide selection of laser lines, high optical efficiency, high energy generation for certain diagnostic and therapeutic procedures, well established relationships between the absorption of monochromatic lines and the identification of selected tissue and bones, and favorable reflection characteristics of selected lines for optimum contrast in obtaining an image.

The video laser camera (VLC) 12 preferably comprises a high resolution, wide dynamic-range digital video imager 22 comprising an image buffer/processing system. The VLC 12 also preferably includes lasers 24 and an associated laser beam control 26 capable of simultaneously delivering localized independent laser radiation for therapy. The VLC 12 preferably avoids the loss of contrast from scattered radiation that exists When an object is illuminated with white light over its full surface during an exposure as characteristic of conventional photography or television. The VLC 12 illuminates an object locally as the laser scans through a raster. Each raster pixel is recorded in succession. Consequently, the recorded pixel is not subject to the loss of contrast inherent in conventional video imaging which loss is principally due to radiation scattered from other pixels.

One suitable VLC 12 is a digital laser scanning fundus camera such as disclosed by A. Plesch et al, in an article entitled "Digital Laser Scanning Fundus Cameras", *Journal of Applied Optics*, Apr. 15, 1987, Volume 26, No. 8. The latter VLC employs an air-cooled Argon laser. The laser generates a beam passing through two microscopic objectives to shape the beam and to define a shutter. The raster generator comprises a polygon mirror scanner and a linear galvanometer scanner. The illuminating beam is horizontally deflected by an eighteen-face polygon mirror scanner rotating at approximately 52,100 rpm. The exit plane of the polygon scanner is projected on a scanning plane by a confocal arrangement of two camera lens systems and a General Scanning linear galvanometer. The scanner deflects the illuminating beam vertically with a repetition rate of 50 hertz on a fly-back time of 2 ms. A second symmetrical arrangement of two camera objective lenses projects the laser beam via a semi-transparent mirror of low reflectivity onto the surface of the object to be examined, e.g., the retina of the human eye.

Another suitable VLC 12 is an optical system such as disclosed by Johan S. Ploem in an article entitled, "Laser Scanning Florescence Microscopy", *Journal of Applied Optics*, Aug. 15, 1989, Volume 26, No. 16. The disclosed laser scanning system employs a laser beam which is expanded with a telescope to a size suitable for microscope objective lenses. The laser beam is displaced along two axes by an X-Y scanner unit consisting of two orthogonal galvanometer scanners. A pair of mirrors are interposed in the optical path. The beam is focused by a diffraction-limited spot on the object. Illuminated light is collected by the microscope condenser and directed to a photomultiplier tube. For florescence and reflectance microscopy applications, a light path retraces the entire illumination beam path in reverse, including the scanning mirrors, until the reflected beam is reflected by a beam splitter onto a photomultiplier tube. The disclosed confocal laser scanning microscopy provides for the imagery of multiple focal layers of the specimen and a three dimensional image reconstruction. Combinations of the images are stored in a computer memory for comparing phase contrast and florescence images of the same area of the specimen to enable multi-parameter analysis of various cells.

Another suitable VLC 12 may be similar to the confocal microscope disclosed by W. B. Amos et al, in an article entitled, "Use of Confocal Imaging in the Study of Biological Structures", *Journal of Applied Optics*, Aug. 15, 1987, Volume 26, No. 16. Light passes from a laser into a reflector. The reflector is a chromatic reflector for florescence microscopy or a half-silvered mirror for reflection imaging. The optical scanning system directs a parallel beam of light into the eyepiece of a conventional microscope. The beam is focused to a diffraction-limited spot in the specimen. Light reflected or emitted by the specimen returns along the original illumination path and is separated from the incident light at the reflector.

A schematic block diagram of the principal components of a generalized VLC 12 and the endoscope 10 which comprise the overall endoscopic/camera system is illustrated in FIG. 3. The endoscope is bi-directionally optically coupled to the VLC by an optical coupler 28 which may comprise any of a number of optical components. The video signal from the endoscope returns via the optical coupler 28 and is applied to a photosensor such as a photomultiplier 30 or one or more elemental detectors for transmission to the digital image acquisition and processing system 22. The acquisition and processing system 22 may be integrated into camera 12 or may be a separate unit. The video output signal from the camera may be transmitted to a work station 32 The work station 32 typically may be a console with interactive displays. The received video signals can be manipulated and studied by the diagnostician at the work station 32. The signals from the camera may also be cast into data form and transmitted to and from an archival storage 34.

It should be clear that the video signal from the photomultiplier or elemental detectors can be fed to an analog display system for direct viewing when the image acquisition is in real time.

As will be further described hereinafter, the VLC and the endoscope cooperate to provide a system wherein, in addition to an imaging beam, a separate therapeutic laser beam generated by laser 24 of the camera is transmitted through the endoscope. The therapeutic beam is projected upon a selected location on the surface of the object or tissue under examination, and the tissue is concurrently continuously monitored through the imaging optics system of the camera. The therapy beam can be precisely controlled by beam positional control 26 so that any localized region of the object being visually examined may be effectively treated without requiring repositioning of the probe end of the endoscope. In preferred form, the therapeutic laser 24 and the control 26 are integrated into the VLC 12. The V 12 can be configured to include as many lasers as required to provide requisite monochromatic wavelengths and power for illumination as well as therapy. The VLC can be employed for florescence imaging, i.e., with procedures where the incident radiation beam is in one wavelength and the imaging is accomplished with florescence radiation. The laser radiation, in some cases, can be employed when sufficient numbers of monochromatic lines are available in a manner similar to the illumination from a monochrometer with the system operating as a powerful scanning spectrophotometer. The VLC 12 also provides a high spacial resolution and a wide dynamic range, thereby permitting correlation between spacial features and spectral signatures.

Figure 2:
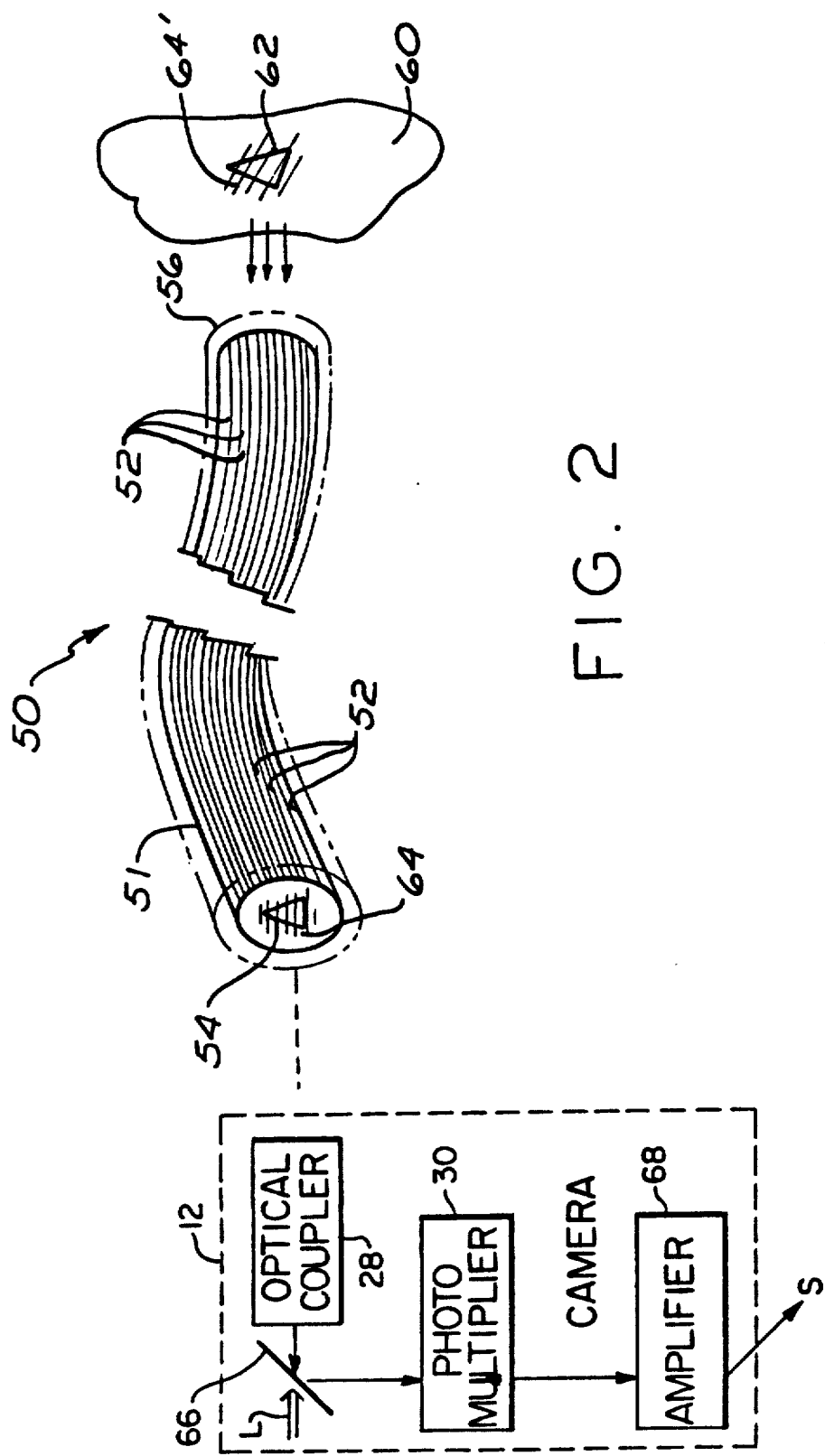
FIG. 2 is a schematic view illustrating the operation of the endoscope of FIG. 1 in conjunction with a video optical camera system in accordance with the present invention.

With reference to FIG. 2, one embodiment of an endoscope 10 comprises an elongated flexible tubular probe 50. Probe 50 is formed of flexible plastic, rubber or other conventional materials. A flexible coherent fiber optics bundle 51 comprising a multiplicity of optical fibers 52 traverses the length of the probe from the proximal end 54 to the distal probe end 56. In the region adjacent to the proximal and distal ends, the coherent fiber bundle 51 is essentially rigid. The fibers 52 at the bundle ends are fused into the shape of a solid small cylindrical segment so that the individual fibers 52 of the bundle maintain their spacial relationship or coherency.

The probe 50 is illustrated in relation to a body or tissue section 60 to be examined. The distal end 56 of the probe is positioned in close proximity to tissue section 60 by conventional means. The specific object (illustrated as a triangle) of the body section which is to be imaged by the endoscope is designated by the numeral 62. Monochromatic illumination light (L) from a laser raster scanner impinges a beam splitter 66 of a camera 12 for projecting an input raster 64 from the laser scanner onto the proximal end 54 of the probe 50. The light traverses the fiber optics bundle 51 of the probe and is projected through the distal end 56 so as to trace a raster 64' onto the surface of the object 62 to be examined. The raster light scans over the surface of the object in a serial fashion.

Reflected light from the object 62 returns in the direction of the FIG. 2 arrows through the fiber optics bundle and strikes the beam splitter 66 of camera 12. The reflected light is sensed by a photomultiplier 30 whose output is fed to a video amplifier 68. The amplifier 68 transmits an electrical video signal(s), which at a given instant of time, is proportional to the quantity of light reflected from the point on the surface of the object 62 to which the laser beam raster is projected. The electronic video signal can then be transmitted to an analog system for recording and display or to a digital imaging system for recording, processing and display.

The latter described endoscope essentially employs a single fiber optics channel and does not require separate illumination and imaging channels. Moreover, by integrating the endoscope optical paths of the therapy laser beam with the imaging laser beam, the requirement of a separate therapeutic channel to carry secondary laser radiation may also be eliminated. Consequently, the endoscope comprising probe 50 has particular applicability in connection with endoscopes for very small diameter applications such as required in the imaging of coronary arteries. Many of the conventional problems associated with high-powered light requirements are solved by lasers having a sufficient power to provide the selected monochromatic radiation to thereby operate in a far more efficient manner than conventional light sources. An additional advantage of the endoscope lies in the scatter reduction and the contrast improvement which is realized by recording the reflected radiation from successive localized pixels imaged as the beam serially progresses through a raster. The raster scanning process avoids the inherent problem of contrast loss through scatter that ordinarily prevails when illuminating the entire surface of an object and recording the image at the same time. In conventional endoscope optic systems, scattered radiation from one pixel is commonly detected in another imaged pixel to thereby reduce the intrinsic imaging signal. In addition, antireflection coatings can be applied to the optical fibers with a high degree of precision. The coatings minimize loss of contrast with a scanner employing monochromatic radiation compared to loss of contrast with a scanner employing a customary white light source. Consequently, the endoscope of FIG. 2 is particularly advantageous for applications wherein an image may be suitably observed by illumination of a single monochromatic laser line.

Figure 4:
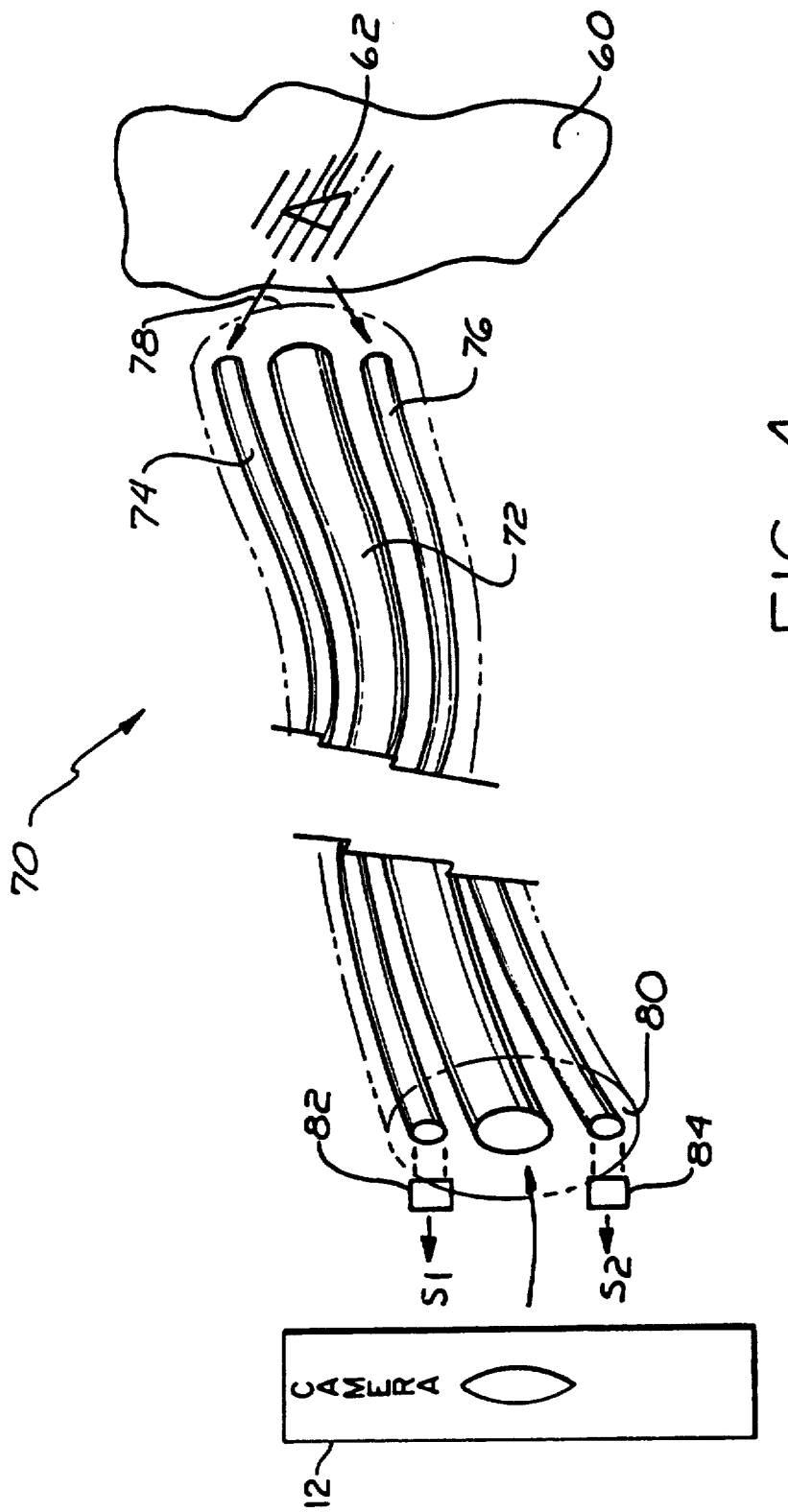
FIG. 4 is a schematic view of a second embodiment of an endoscope and an associated optical system in accordance with the present invention.

With reference to FIG. 4, the endoscope probe 70 has a central flexible fiber optic bundle 72 for raster illumination of the object 62 of tissue to be examined. A pair of diametrically opposed light channels 74 and 76 of optical fibers extend longitudinally parallel to bundle 72 to transmit the reflected radiation from the object 62 along an optical path extending from the distal probe end 78 to the proximal end 80 of the endoscope. Photodetectors 82 and 84 are positioned at the proximal ends of the light channels 74 and 76, respectively. The reflected radiation transmitted through the light channels impinges the photodetectors 82 and 84. The photodetectors 82 and 84 in turn generate electrical video signals $S_1$ and $S_2$ for processing as previously described.

The monochromatic light from the laser raster scanner 20 and laser therapy positioner 26 is applied at the proximal end 80 of the fiber optics bundle 72. The endoscope of FIG. 4 does not employ a beam splitter. Consequently, reflections from the proximal input surface of the fiber optics bundle 72 are minimized. Reflections are also encountered in connection with beam splitters. In addition, the problem of veiling glare associated with multiple optical components in an imaging chain may also be substantially reduced by the elimination of the beam splitter. Short time constant photodetectors are preferably employed so that the time lag characteristic which conventionally prevails in conventional endoscopic optical systems using video tubes is avoided.

Because two detector illumination channels 74 and 76 are employed with each illumination channel having its own photodetectors 82 and 84, two images in the form of signals $S_1$ and $S_2$ can be acquired independently. The images acquired may be from two widely separated spectral region, such as the UV and IR, if desired.

Figure 5:
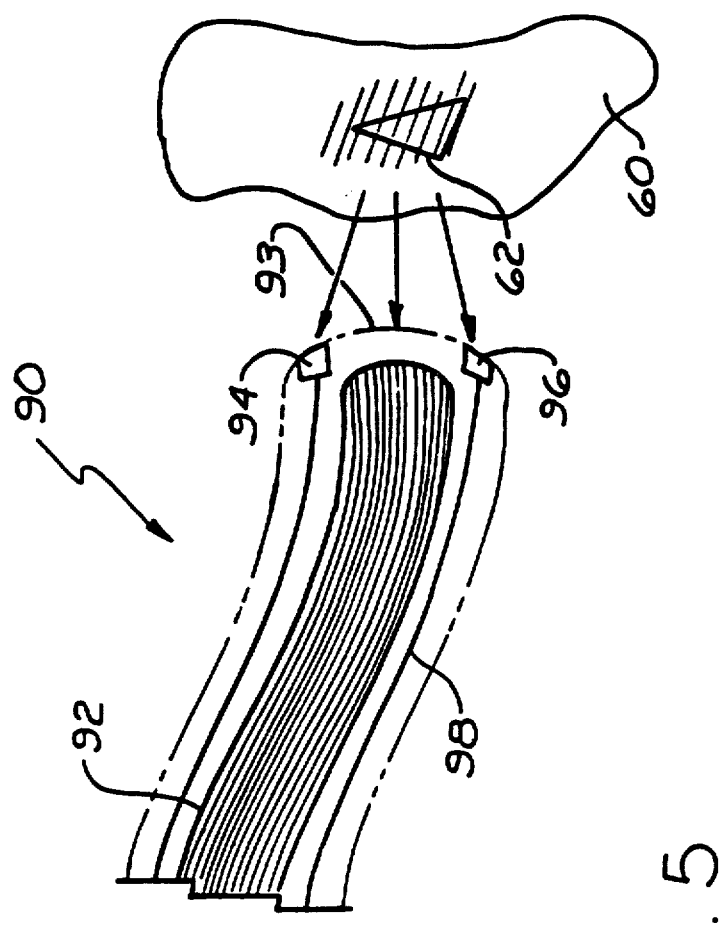
FIG. 5 is a schematic view of a third embodiment of an endoscope and an associated optical system in accordance with the present invention.
Figure 5:
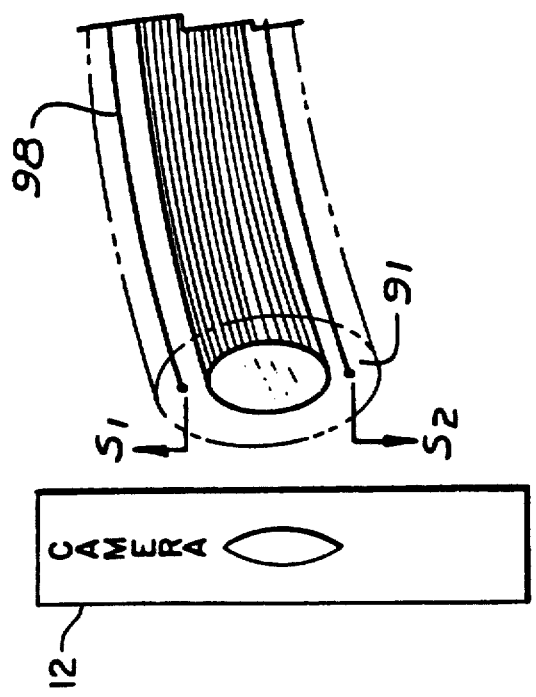

With reference to FIG. 5, endoscope probe 90 has a central coherent fiber optics bundle 92 which extends longitudinally from the proximal end 91 to the distal and 93. The fiber optics bundle 92 functions as previously described to project a video raster 64' onto the object 62 to be examined. Elemental photodetectors 94 and 96 are mounted at the distal probe end 93 of the endoscope for detecting incident reflected radiation from the object 62. Wires 98 extend the length of the endoscope for carrying the electrical bias and the signal current from the elemental photodetectors 94 and 96. The electrical video signals $S_1$ and $S_2$ communicate via the electrical wires 98 with the circuitry for processing the video signal.

It should be appreciated that endoscope probe 90 does not require separate optical detector and illumination channels since the elemental photodetectors 94 and 96 are located at the distal end 93 of the endoscope. As the illumination beam scans out a raster, the video signal is generated in a highly efficient manner since the photodetectors are positioned in an optimal location in the immediate vicinity of the object 62 to be examined. The photodetectors 94 and 96 may be relatively small in dimensions. Thus, the diameter of the endoscope probe 90 may be relatively small. As will be described in detail hereinafter, the photodetectors 94 and 96 may be lateral effect diodes. Three dimensional images may be obtained from embodiments which employ lateral effect diodes. Several photodetectors may be positioned at the distal end of the probe. The photodetectors may be configured into shapes which are circular, square, rectangular, polygonal, or other shapes as desired.

An endoscope comprising probe 90 avoids the loss of optical transmission through the illumination channels. Quartz fibers typically provide optical transmission throughout the spectrum range for a wide variety of applications between 3,000 Angstroms and 2 microns. The elemental photodetectors can be selected so as to operate in the spectral range from 3,000 to 20,000 Angstroms. One or more small photodetectors can be selected and suitably positioned at the distal probe surface of the endoscope to specifically respond to whatever radiation is selected for the imaging and therapy, regardless of the wavelength of the reflected radiation. It should be appreciated that a given endoscope, as described, is suitable for UV imaging as well as for imaging at two microns. The endoscope probe 90 offers wide range of spectral response. For example, signal $S_1$ may be responsive to reflected radiation imaging in one given spectral region and signal $S_2$ may be responsive to reflected laser therapy radiation in another spectral region. Endoscope probe 90 is also adaptable for multi-spectral imaging for contrast enhancement for a given endoscope. Photodetectors 94 and 96 which are suitable for the described endoscope can be fabricated from materials such as crystalline silicon, amorphous silicon, cadmium sulfide and lead sulfide. For operation in the ultra-violet through the visible spectrum, into the near infra-red, the photodetectors as described provide extremely reliable performance at body or room temperatures. Combinations of infra-red transmitting fiber and cooled photodetectors may also be employed for infra-red applications. Uncooled thermal detectors which offer less performance may be satisfactory for some infra-red applications.

The laser camera system, as described, may function as an imaging scanner spectrophotometer by using one or more photodetectors with their spectral responses matched to that required for the given spectrum encompassed in an application. The relative spectral reflectance for each pixel in an image can be measured for a given imaging radiation. By precise calibration, absolute reflectance values can be obtained.

The laser therapy can be effectively accomplished with the described video laser camera systems and endoscopes. If a given laser line is best suited for a given therapy, the laser line can be transmitted through one or more of the fibers to the object requiring treatment. The number of selected fibers defines the composite therapy beam diameter. For example, if a lesion on the surface of the object is imaged by ten to twenty fibers, then the laser radiation for therapy could be channeled through the same fibers of bundle 92 to cover the designated lesion area. Simultaneous imaging may also be accomplished through the same fibers consistent with the raster scanner operation. The secondary therapeutic radiation generated by laser 24 can be shuttled back and forth through the fiber optic bundles or even pulsed through one or more fibers to minimize possible heating problems. Heating, in general, is ordinarily not a critical problem, since high-temperature glass fibers have been developed which operate at temperatures up to 800° Fahrenheit. Quartz fibers have an even higher temperature operational limit.

For the described endoscopic systems, there are two principal operational techniques wherein the secondary therapy irradiation of an object can be accomplished simultaneously with viewing the reaction of the object to the irradiation treatment. In one technique, both the imaging beam and secondary therapy beam pass through the scanning system. Such an approach requires that the secondary therapy beam be pulsed in synchronization with the scanning raster so that the secondary therapy beam is delivered in a precise manner. The first approach requires that the precise timing of the imaging pulses and therapeutic laser pulses be coordinated.

In a second technique, the high-energy irradiation is transmitted by a second separate optical system. This second general approach does not require the pulsing of the therapeutic beam and synchronization of the scanning of the raster. However, the imaging channels might need to be filtered so that the secondary irradiation does not interfere with the imaging process. Consequently, photodetectors employed in such a system could require sufficient filtering so that the photodetectors selectively respond only to radiation from the imaging beam. For endoscope probes 70 and 90, which employ multiple detectors, one or more of the photodetectors may be employed to sense (view) the imaging radiation while being opaque (blind) to the therapy radiation. By the proper selection of the photodetector and the filter, detectors may be employed to monitor the level of reflected radiation with time as the therapy beam causes a change in the reflectance properties of the object or tissue on which the high-energy beam is focused.

Spectral selective viewing of a structure below an object surface can be obtained since the images obtained from different laser wavelengths can in certain cases represent different depths of penetration below the surface of an object. Tomographic planes may thus be constructed.

Contrast enhancement can also be obtained by multi-spectral imaging. The multi-spectral imaging is accomplished by means of employing photodetectors having different defined spectral responses. Processing of the electrical video signals may be accomplished by means of energy subtraction techniques such as are employed in digital radiology and red-near infra-red subtraction techniques employed in diaphranography of the breast.

Figure 6:
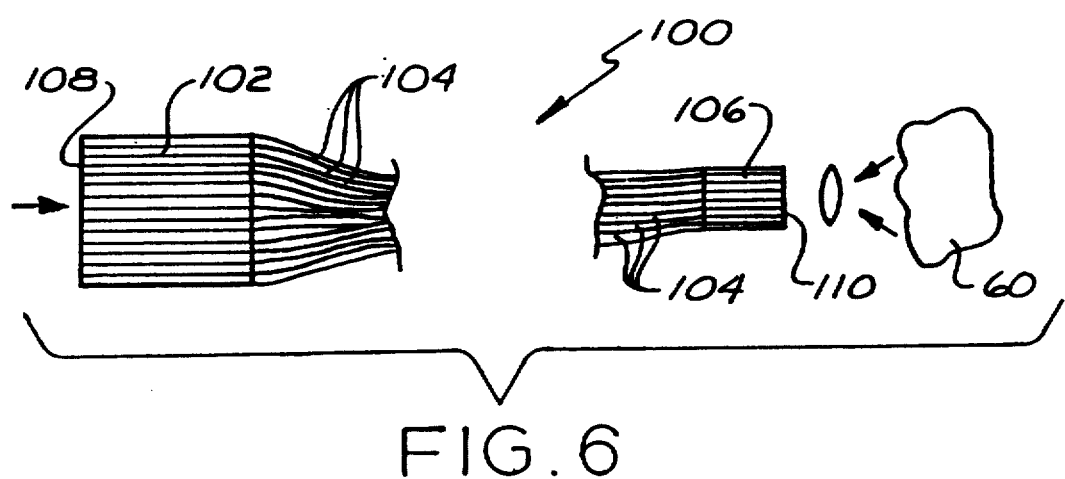
FIG. 6 is a fragmentary side view, partly in schematic, illustrating a fiber optic bundle for an endoscope in accordance with the present invention.

With reference to FIG. 6, one embodiment of a rigid coherent fiber optics bundle 100 for an endoscope as previously described comprises a proximal cylinder 102 consisting of fused strands of substantially identical optical fibers 104. Likewise, a distal cylinder 106 comprising fused strands of the fibers is formed at the distal end of the endoscope. The diameters of the fibers of the proximal cylinder 102 are significantly larger than the associated corresponding optical fiber diameters of the dista cylinder. The optical fibers 104 may have a substantially constant taper from the proximal to distal ends. Thus, the individual fibers 104 may be described as elongated truncated cones. Alternatively, the taper may be formed within the fused cylinder.

Optical radiation from the optical raster scanner is projected onto the input surface 108 of the proximal cylinder 102. The relatively large input surface 108 defined by the proximal end of the fibers 104 functions to provide large heat capacity, means for cooling, and a better ability to withstand damage from intense laser radiation at optics bundle 100. In conventional endoscopes, high-energy laser radiation frequently does often result in fiber damage, particularly at the proximal end of the endoscope fibers. Because the flexible optical fibers are selected to be highly transmissive, the fibers are not particularly subject to appreciable increases in temperature unless there are localized impurities. However, the proximal cylinder 102 is susceptible to damage in large part because of the high absorption in the cladding material which leads to excessively high temperature and damage from thermal shock. By constructing the fiber diameters at the input surface 108 to be much larger than the fiber diameters at the output surface 110, the potential for thermal shock can be diminished. Thus, all other relevant physical characteristics of bundle 100 being equal, the energy density of a laser beam transmitted through fiber bundle 100 could be considerably increased and the heat capacity input considerably increased while decreasing the potential damage to the fiber optics bundle. For example, for a bundle 100 where the diameter of the input surface 108 to the output surface 110 is 10 to 1, a 10 micron flexible fiber optic bundle could have an effective input of 100 microns.

Figure 7:
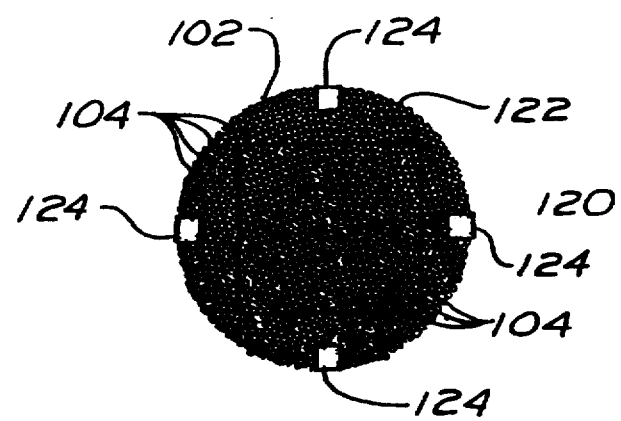
FIG. 7 is an enlarged end view of the endoscope proximal optic bundle of FIG. 6.

For procedures which involve multi-spectral imaging, surface tomography, different spectral responses and different perspectives, multiple detectors may be required. Such detectors may be efficiently arranged and mounted at the proximal end outer region of the fiber optics bundle as illustrated in FIG. 7. For the configuration 120 illustrated in FIG. 7, the boundary (schematically illustrated) of the raster which is projected onto the proximal cylinder encompasses only a central portion of the entire cross-sectional extent of the fiber optics bundle. Accordingly, an outer ring 122 of fibers is available for coupling to the photodetectors 124. Essentially, the central raster illumination transmission zone, defined by boundary 120, is encircled by a concentric ring 122 of fiber channels. The fibers in the ring 122 Can be employed, either individually or collectively in groups, to transmit the reflected radiation from the tissue surface illuminated by the laser radiation near the distal end of the endoscope probe back to the photodetectors 124, which are located at the proximal end.

In one example, the diameter of the input proximal end 108 of the fiber optic bundle 100 is four millimeters, and the diameter at the distal probe end 110 is one millimeter. The effective de-magnification of the fiber optics bundle 100 is approximately four. An individual fiber at the proximal end having a diameter of 40 microns has a corresponding diameter at the distal end of 10 microns.

If a laser raster defined by a square boundary 120 having a diagonal dimension of two millimeters is centrally projected on the proximal surface 108, a one millimeter thick ring 122 of fibers remain to function as the optical channels for photodetection. Such a ring could accommodate twelve detectors 124 in side-by-side orientation having dimensions of approximately one-by-one millimeter. The specific shape and dimensions of the detectors 124 could be suitably varied in accordance with the requirements of a specific application.

A laser raster scanner system as described can be employed in conjunction with multiple photodetectors to provide multi-spectral imaging. For example, an Nd:YAG laser which generates the typical line at 1.064 microns and a strong line at 1.318 microns can be coupled to different elemental photodetectors. Each of the elemental photodetectors is responsive to one of the laser lines so that the object under examination can be imaged simultaneously with both lines. For example, a laser system, such as described by R. A. Morgan, "Nd:YAG Laser For the Study and Application of Non-Linear Optical Crystals", *Optical Engineering*, Volume 26, Pages 1240–1244, 1987, when suitably coupled with non-linear optical crystals, can permit simultaneous generation of frequencies extending throughout the visible spectrum, including the three primary colors and into the near ultra-violet range.

Figure 8:
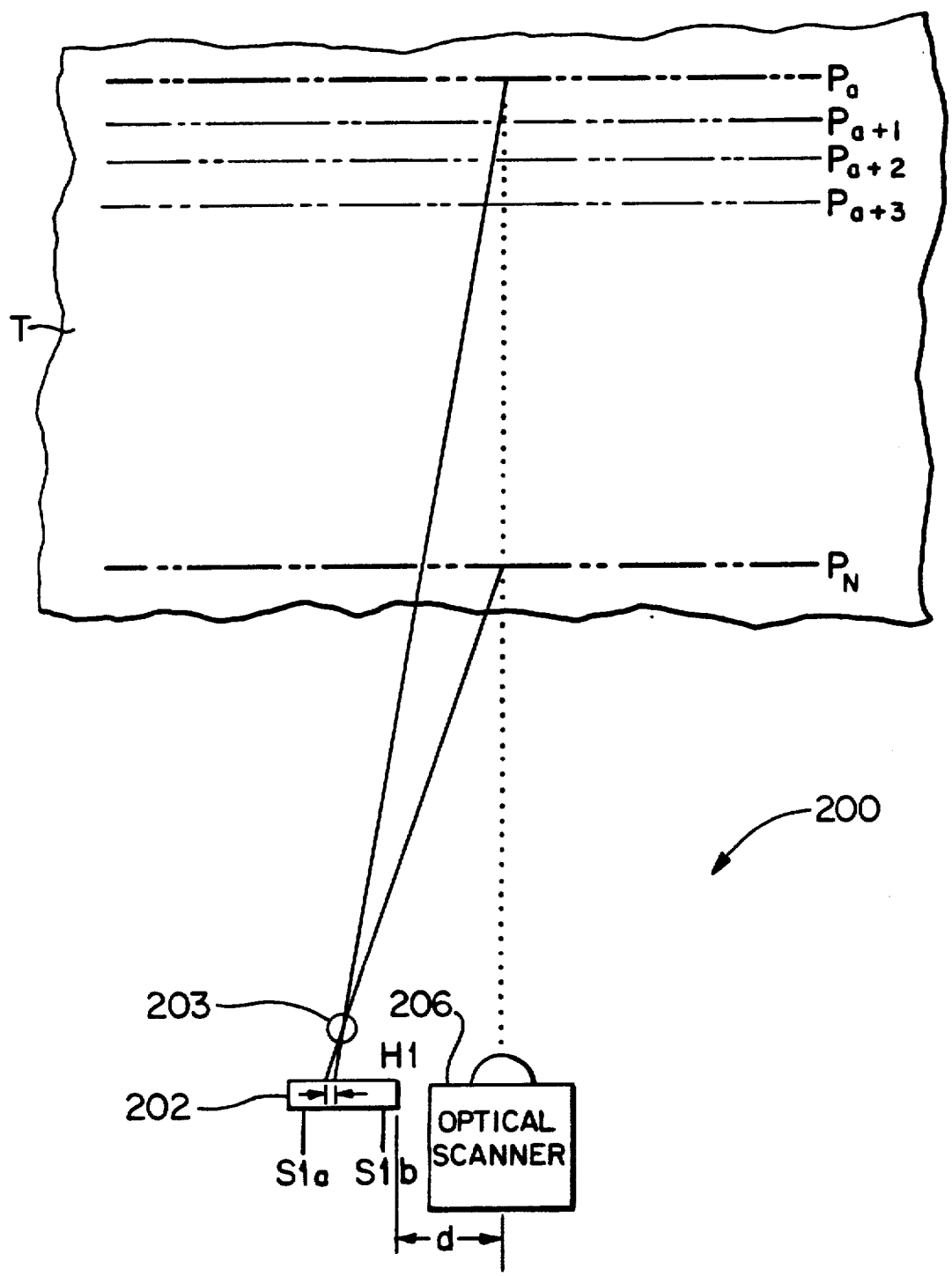
FIG. 8 is a schematic view of a multi-dimensional imaging system in accordance with the present invention.

With reference to FIG. 8, a three dimensional image acquisition system in accordance with the present invention, is generally designated by the numeral 200. Image acquisition system 200 employes a single lateral effect diode 202. The optical raster scanner 206 projects an illumination spot on the test object T to be imaged and traces out a raster as previously described. The precise angular projection of the raster beam is known for every pixel that the scanner illuminates throughout the tracing of the raster.

The lateral effect diode 202 detects the reflected illumination from the object through the optical center of lens 203. For a given separation distance d between the photodiode and the central axis of the raster, every pixel illuminated in image plane $P_a$, as the raster is scanned, corresponds to a unique positional point detected by the lateral effect photodiode. Likewise, every pixel illuminated by the scanner in image plane $P_N$, corresponds to a unique positional point detected by the lateral effect photodiode.

Unique positional points can thus be extrapolated for a continuum of planes $P_{a+1}, P_{a+2}, P_{a+3}, \ldots$ which correspond to each pixel illuminated by the optical raster scanner for the given plane. The depth resolution is defined by the separation distance d and the signal to noise ratio of the lateral effect photodiode 202. The depth resolution parameter which is a function of the illumination received by the photodetector, determines the number of distinct spacial shifts that the photodiode can resolve. The distinct spacial shifts define the depth resolution.

Figure 10:
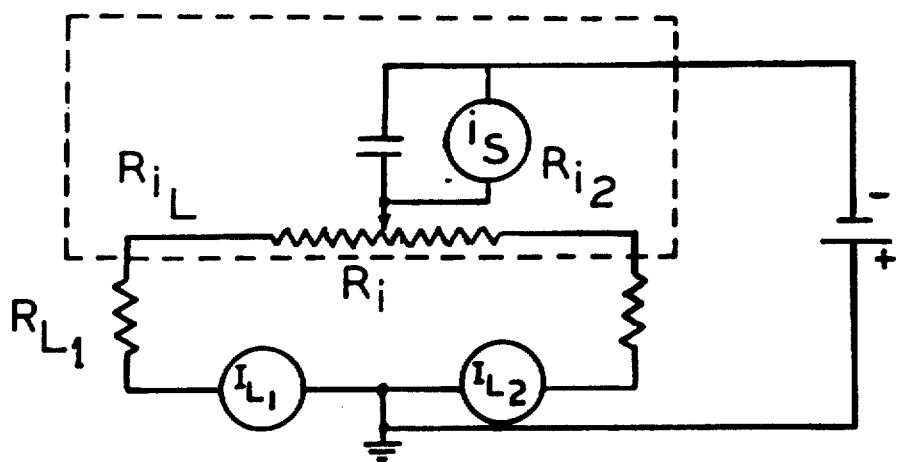
FIG. 10 is a simplified schematic circuit diagram for a lateral effect photodiode employed in the imaging system of FIG. 8.
Figure 11:
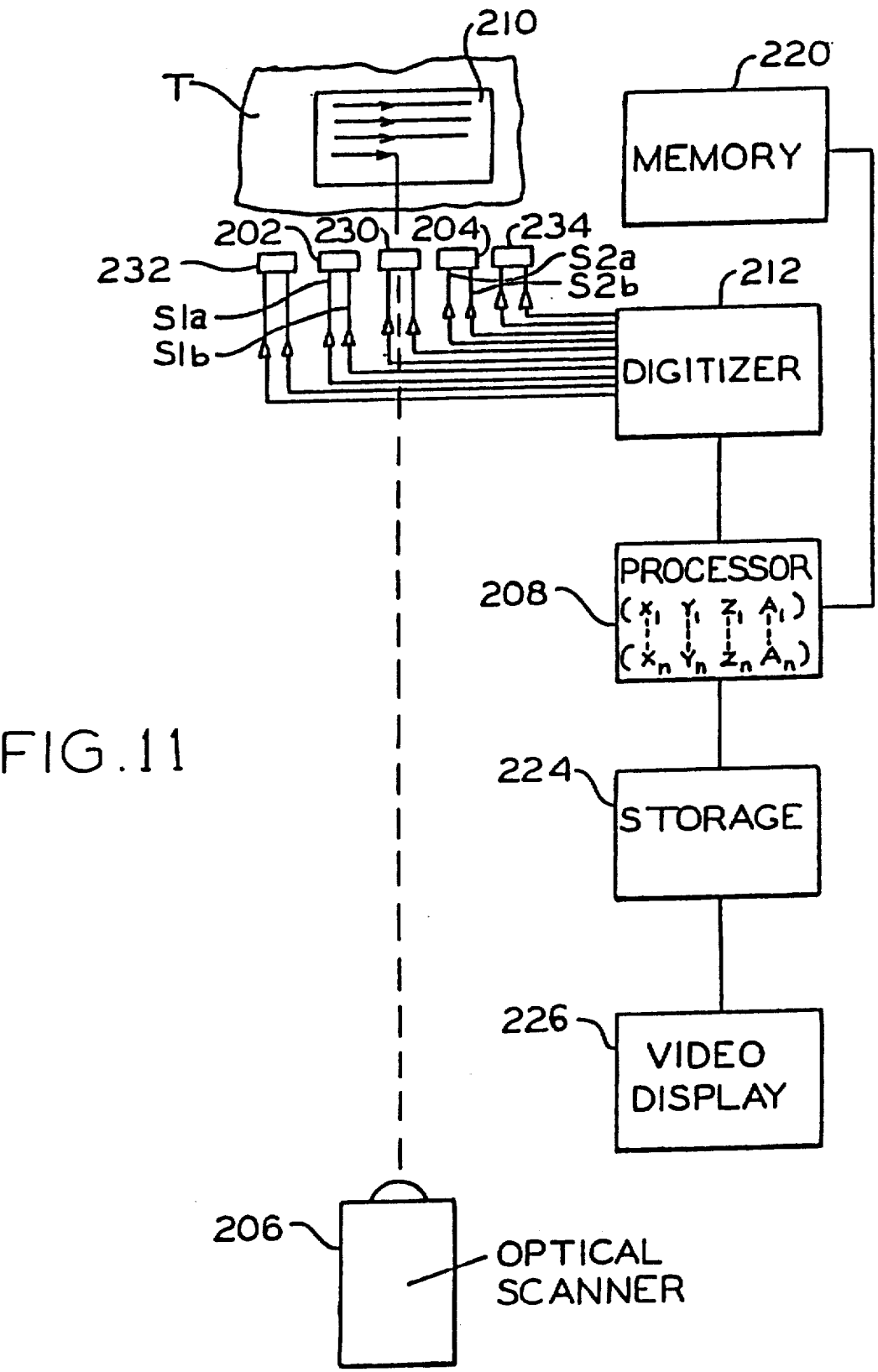
FIG. 11 is a schematic diagram illustrating a multi-dimensional image acquisition system in accordance with the present invention.
Figure 12:
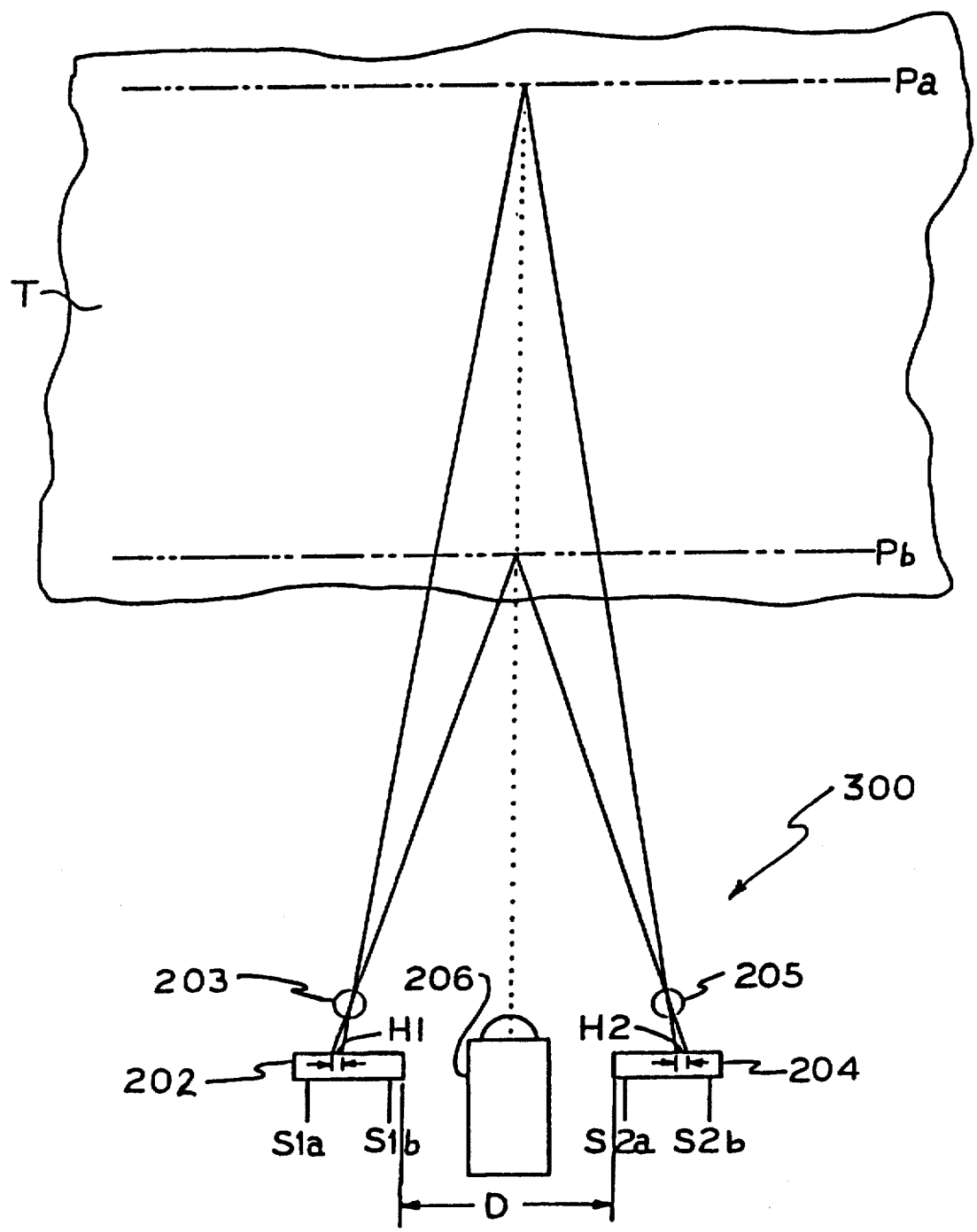
FIG. 12 is a schematic view of another embodiment of a multi-dimensional imaging system using two lateral effect photodiodes in accordance with the present invention.

With reference to FIGS. 8 through 12, a three dimensional image acquisition system according to the present invention is generally designated by the numeral 200 or 300. The image acquisition system 200 in FIG. 8 employs one lateral effect photodiode, and photodiode system 300 in FIG. 12 employs two spaced lateral effect photodiodes 202 and 204. The lateral effect photodiodes are employed in conjunction with an optical raster scanner 206 to generate signals indicative of detected radiation intensity and position for an object to be imaged in three dimensions. The photodiodes 202 and 204 in the system 300 of FIG. 12 are typically identical. A processor 208 (FIG. 11) electrically communicates with the lateral effect diodes to generate data which may be employed for generating three dimensional images of an object. The data can be processed and viewed in a variety of display technologies such as stereo monitor projections, synchronized shutter glasses, or by creating multiple perspective views for frame by frame or real time "fly by" presentations.

The optical raster scanner camera system 206 employs a radiation source which generates a beam of radiation. The beam is directed to an optical deflection system that scans out a raster 210 in two dimensions for a projection on test object T. (see FIG. 11). The illumination raster is similar to the raster geometry used in television systems. As previously discussed, one suitable type of deflection system uses a galvanometer controlled mirror for the slower vertical deflection and a high speed rotating polygon mirror to generate the horizontal beam deflection. Another system uses galvanometers to generate both the horizontal and vertical deflections. The two dimensional illumination raster pattern is formed when the beam is projected through either of the deflection systems. As noted above, the radiation can have a spectral content that can range from the ultra-violet through the visible into the infra-red. The only limitations on the nature of the radiation is that it behave according t the laws of optics in regard to refracting and reflecting processes; i.e., it must properly be reflected off the scanner deflecting mirror surfaces and the test object T and refracted through the lenses 203 and 205 respectively positioned in front of the position sensing detectors 202 and 204. The detection system comprising one or more lateral effect photodiodes 202 and 204 directly senses radiation reflected from the object T on a pixel by pixel basis.

The use of two or more lateral effect photodetectors can be attractive when the beam sweeps a wide angle, so that there could be unacceptable loss of signal for far off-axis imaging. Alternatively, this data can be used subsequently to create multiple perspective views of the surface topography of the object scenes being imaged. Perspective views similar to the binocular vision angles can also be generated for presentation on a stereo display system 226.

The geometrical and mathematical basis for stereo imaging are illustrated in the simplified representation in FIG. 8. FIG. 8 represents a view from the perspective of the Z axis of test object T, i.e., if viewed from directly above the photodetector 202 which can provide a three dimensional image of the scene in front of the system. On the other hand, in conventional stereoscopic imaging, two area detectors (e.g., TV cameras, eyes) view the scene from the same plane but with a horizontal space between them. All points in the scene are imaged through focus centers. Points that are located in one image plane are correspondingly imaged onto the two camera sensors through the focus centers. All points in the one plane have a precise correlation because they are imaged on each camera. Points in a second image plane will correspondingly be imaged through the focus centers onto each camera. There is a distinct horizontal shift of points at the second image plane relative to those which are imaging the corresponding points of the first image plane.

Figure 9:
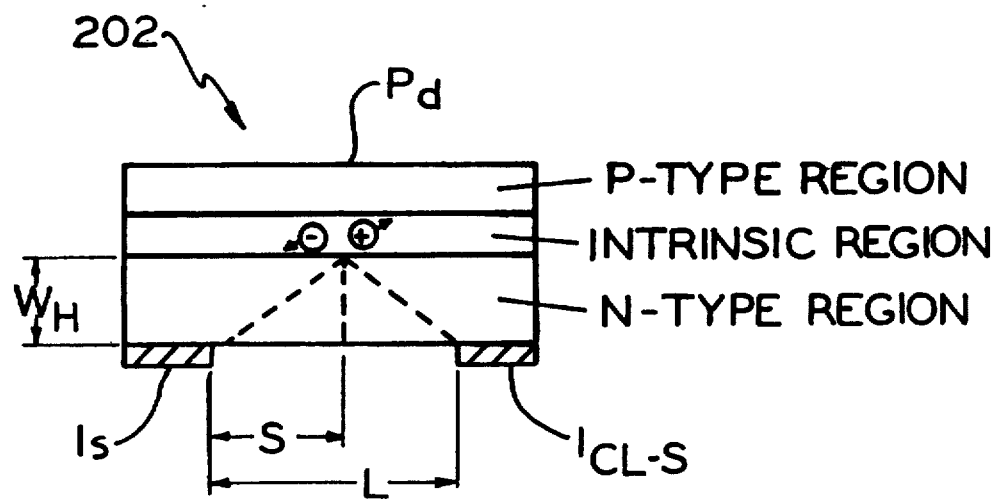
FIG. 9 is an enlarged cross sectional diagram, partly in schematic, of a lateral effect diode employed in the imaging system of FIG. 8.

The general operation of the lateral effect photodiode 202 which makes it suitable for three dimensional imaging is illustrated in FIGS. 9 and 10. The basic difference between a standard photodiode and lateral effect photodiode 202 is the contact arrangement as shown in the single axis version of FIG. 9. Dependent on the position of the incident light beam, an Ohm's Law split of the carriers generated by photo absorption in the substrate between the contacts provides precise positional information of the illumination point.

Referring to the equivalent circuit in FIG. 10, when a ray of light strikes the lateral effect photodiode (at a contact point), a constant current is generated in the bulk substrate resistivity modeled as Is. The constant is split between the two paths, e.g., the first path being $R_{I1} - R_{L1}$ and the second path being $R_{I2} - R_{L2}$. Now if $R_{I1} >> R_{L1}$ and $R_{I2} >> R_{L2}$, and $R_{L1} = R_{L2}$, then the current flow in each path is proportional to the Ohm's Law split of the sheet resistance of the detector. To calculate the position of the point of light, the center point is treated as zero. Therefore, subtracting the current in one path from the other will result in a null reading in the center when equal current flows in each path. Therefore, in general:

$$Position = I_{L1} - I_{L2}$$

Finally, to eliminate the dependence of the positional information from the total amount of illumination, the positional signal is then normalized with respect to the total current flow.

$$Position = (I_{L1} - I_{L2})/(I_{L1} + I_{L2})$$

Referring to FIG. 8, as the beam scans the surface of the object in the horizontal plane, the lateral effect photodiode 202 essentially senses the same positional information if the elevation of object T is all at the same plane. There may be some non-linearity due to the optics as the beam scans off-axis. The non-linearity can be corrected in the optic system. Alternatively, the non-linearity can be more effectively corrected by mapping the non-linearity as a function of the beam position and storing the data in a digital memory 220. The non-linearity can then be deconvolved by applying the inverse mapping function to the signal information.

Spatial shifts H sensed by the photodetector correspond to changes in elevation (depth). In practice, the non-linearities associated with a topography can be accounted for by mapping out the elevation differentials across a known three dimensional test object versus the position shift read out from the detector 202 diode, employs positional information and the intensity generated by the lateral effect photodiode 202 for each pixel scanned by the optical scanner. Calibration scans for flat image planes at various depth increments are employed to generate a mapping function which maps the depth for each pixel. The mapping function is also employed to remove non-linearities in the detection system.

A single lateral effect diode thus may be employed to generate three dimensional image data including a surface map or image of both the illumination intensity and the elevation or depth data of the test object being imaged. The image may be acquired at a high speed and can have various sizes or dimensions such as, for example, a few lines for a range finding mode or thousands of lines for a complete image data set for a given region.

The lateral effect photodiode generates the positional signals S1a and S1b as previously described. The sum of the signals corresponds to the intensity data of the reflected illumination from the object. The difference of the signals corresponds to the positional angle of the illumination. Using the signals from the single lateral effect diode 202, a three dimensional matrix, including intensity data for each pixel and a depth for each pixel in the scanned object or scene, can be derived. It should be appreciated that other standard photodiodes (not illustrated) can also be employed to detect the intensity. The intensity may be optimized for other parameters such as spectral response.

An image acquisition system such as illustrated in FIG. 8 is responsive to input from a single lateral effect photodetector 202.

In the two detector system of FIG. 12, the elevation or third coordinate information, which corresponds to the spatial shifts of the detected signals originates as the difference between the position signals sensed by the two detectors. The spacing D between the detectors 202 and 204 as well as the angle that their normals subtend to the object determines a zero elevation (depth) plane. Small elevation changes in the object scene (such as image planes Pa and Pb) correspond to small horizontal shifts H1 and H2 in imaging points on the surface of the imaging sensors 202 and 204. If the detector normals are perpendicular to the object space, then infinity is essentially the reference elevation (depth) plane. In medical imaging application such as endoscopy where the object distance is only a few centimeters away, the detectors 202 and 204 may be angled towards the center axis. This orientation will reduce the optical non-linearity and establish a new zero elevation reference plane where the detector normals intersect.

At constant elevation planes, the two diodes 202 and 204 will detect the same two dimensional plane information (after the non-linearity has been corrected), as the beam scans from side to side of the raster. The relative elevation (depth) is then calculated as the difference between the positional information sensed by the two detectors and can be derived from the signal output at each of the electrodes in accordance with the following equation:

$$\text{Elevation} = \frac{(S1a - S1b)}{(S1a + S1b)} - \frac{(S2a - S2b)}{(S2a + S2b)} \quad \text{EQ. 1}$$

The individual signals S1a, S1b, S2a and S2b generated from the two signals leads (see $i_S$ and $i_{(L-S)}$ in FIG. 9) on each of the photodetectors is applied to a digitizer 212 immediately following pre-amplification of each output signal. This procedure requires four high speed data streams into the digitizer 212. The elevation (depth) information is then calculated in the processor 208 using Equation 1. The above calculations also may be performed in hardware (either analog or digital). In such cases, only one data stream flows into the digitizer which data stream directly corresponds to the elevation information of each corresponding pixel.

Lateral effect photodiodes are also configured to provide the usual two dimensional as well as depth information. The two dimensional (transverse) information can be obtained from the sum of the currents generated at the electrodes of the lateral effect photodetectors. However, in the simplest system 200 of FIG. 8 only a single one dimensional lateral effect photodiode is required t provide elevation information for the three dimensional image acquisition system 200. The other two dimensions are generated by the conventional scanning raster process.

The signals generated by use of the lateral effect photodiodes provide sufficient information to create an elevational profile of the object scene to be imaged, including an accurate measurement on a point by point basis of the optical signal as the scan progresses. The processor 208 in FIG. 11 generates a matrix relating each three dimensional coordinate (x,y,z) of the object T with an associated photo-intensity A for the coordinate. The information may be placed in storage 224 and/or transmitted to a video display 226. Elevation resolution of the three dimensional imaging system is determined by the horizontal spacing of the detectors 202 and 204 relative to the distance between the detector and image planes, plus the positional resolution of the detector. The latter resolution is principally limited by the limiting noise of the lateral effect photodiodes with their associated pre-amplifiers and their dynamic range characteristics.

With reference to FIG. 11, in addition to the use of the signal information generated, the lateral effect diodes such as 202 and 204, it is possible to simultaneously derive signals from one or more additional conventional elemental photodetectors 230, 232, 234, ... of selected spectral response. Photodetectors 230, 232, 234, ... offer the advantage of permitting the simultaneous acquisition of images in multiple, but isolated spectral regions for purposes of achieving optimal contrast and optimum object identification through multi-spectral imaging, combined with multi-dimensional imaging and image processing. These elemental photodetectors 230, 232, 234, ... may be very small i.e., less than 1 square mm or large solid state detectors, photomultipliers and/or photodiodes selected for their spectral response. The photodetectors may be used with or without the addition of special filters. Images acquired by these additional detectors may be conventional two dimensional images. However, the information derived from photodetectors 230, 232 and 234 can also be coupled to the spatial information obtained from the lateral effect diodes 202 and 204 to provide elevation information in the spectral regions of their response.

In some applications, the detectors 202 and 204 can be positioned relative to the scanner and the scanned object so as to function in transmission rather than reflection. It should also be clear that the spectroscopic image acquisition system 200 can function to respond to luminescence by scanning with a beam of radiation that causes excitation of luminescence in the object being scanned. The latter system can result in a three dimensional image of the distribution of luminescent materials in the scanned object.

Advantages that can be derived from the use of the three dimensional image acquisition systems 200 and 300 ca be obtained in diverse areas such as medicine where instruments such as endoscopes, retinal cameras and microscopes are used to acquire images, and in non-destructive testing where similar instruments may be employed. In particular, the image acquisition systems 200 and 300 provide the advantages of direct acquisition of object elevation information, minimal sensor size, spectral selectivity and scatter rejection.

Spectral selectivity becomes important when spectra is an important factor in acquiring optimum contrast and where multi-spectral imaging can be used to provide a spectral signature as a means of object identification. This mode of operation is well suited to video imaging with the multi-dimensional systems 200 and 300.

The scatter rejection characteristics of the image acquisition systems 200 and 300 are also important when objects to be imaged are immersed in media having suspended particulate matter which function as scattering centers. The optical raster scanner technique inherently minimizes scatter to the photodetector or the photodetectors since the only scatter recorded is that associated with the beam of radiation passing through the medium from the source to the object and the radiation reflected from the surface of the object and directed toward the detector. Consequently, the detected scatter is far less than in conventional imaging where a source of light typically illuminates the full surface of an object, and where scattering may originate from the full field of illumination. Full illumination scattering can cause substantial loss of contrast to photographic or TV acquired images.

While preferred embodiments of the invention have been set forth for purposes of illustration, the foregoing description should not be deemed a limitation of the invention herein. Accordingly, various modifications, adaptations and alternatives may occur to one skilled in the art without departing from the spirit and the scope of the present invention.

What is claimed is:

1. An endoscope adapted for operation in association with optical scanner means which generates radiation tracing out a raster comprising;

probe means for forming a flexible tubular member having a proximal end and a distal end;

first optical cable means disposed in said probe means comprising a bundle of coherent flexible optical fibers forming a first optical cable extending between a proximal end surface and a distal end surface;

photodetector means comprising a photodetector for generating an electrical signal having an instantaneous value proportional to the quantity of light impinging said photodetector;

processor means communicating with said photodetector means for generating a signal indicative of a multi-dimensional image of said object, so that a raster from said scanner applied at said proximal end of said probe means is projected through said distal end surface of said optical channel for illumination of the object to be examined and radiation reflected from the object impinges said photodetector means wherein said processor generates signals indicative of a depth image of said object.

2. The endoscope of claim 1 wherein said photodetector is a lateral effect diode.

3. The endoscope of claim 2 further comprising at least one additional elemental photodetector communicating with the reflected radiation.

4. The endoscope of claim 1 wherein said processor means further comprises matrix means for generating a matrix having a three dimensional coordinate and an associated radiation each pixel of said raster.

5. The endoscope of claim 1 wherein said photodetector is an elemental photodetector.

* * * * *

UNITED STATES PATENT AND TRADEMARK OFFICE
CERTIFICATE OF CORRECTION

PATENT NO. : 5,200,819
DATED : April 6, 1993
INVENTOR(S) : Sol Nudelman and Donald R. Ouimette It is certified that error appears in the above-indentified patent and that said Letters Patent is hereby corrected as shown below:

Column 20, line 30, after "radiation" insert --intensity for--.

Signed and Sealed this

First Day of October, 1996

Attest:

BRUCE LEHMAN

Attesting Officer

Commissioner of Patents and Trademarks